(12) United States Patent
Kitazawa et al.

(10) Patent No.: US 6,552,061 B1
(45) Date of Patent: *Apr. 22, 2003

(54) AMINO ACID DERIVATIVES AND ANTI-INFLAMMATORY AGENTS

(75) Inventors: Manabu Kitazawa, Kawasaki (JP); Keiji Iwasaki, Kawasaki (JP); Eiji Shiojiri, Kawasaki (JP)

(73) Assignee: Ajinomoto Co., Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/285,390

(22) Filed: Apr. 2, 1999

(30) Foreign Application Priority Data

Apr. 2, 1998 (JP) .............................. 10-105336

(51) Int. Cl.[7] ..................... C07C 229/28; C07C 233/08; C07D 233/06
(52) U.S. Cl. ...................... 514/401; 514/559; 514/562; 514/567; 514/618; 514/620; 548/349.1; 560/12; 560/40; 564/162; 564/165
(58) Field of Search ................................. 514/345, 401, 514/559, 562, 567, 618, 620; 548/349.1; 560/12, 40; 564/162, 165

(56) References Cited

U.S. PATENT DOCUMENTS 5,594,012 A * 1/1997 Kitazawa et al. ........... 514/345
5,985,922 A * 11/1999 Kitazawa et al. ........... 514/538

FOREIGN PATENT DOCUMENTS

| DE | 1 238 473 | 4/1967 |
|---|---|---|
| EP | 0 580 378 | 1/1994 |
| EP | 0 869 155 | 10/1998 |
| WO | WO 96/20701 | 7/1996 |

OTHER PUBLICATIONS

Database CAPLUS on STN, Acc. No. 1998: 122615, Hassan et al., 'Synthesis and antimicrobial activity of some new Mannich bases, N–(2–hydroxy–1–naphthyl) amino acid, methyl ester and hydrazide derivatives.' J. Serb. Chem. Soc. (1998), 63(2) pp. 125–130. abs.*
Partial table of contents of J. Serb. Chem. Soc. vol. 63 (1998).*
Database CAPLUS on STN, Acc. No. 1995:215364, Johnson et al., 'N, O–bisFmoc derivatives of N–(2–hydroxy–4–methoxybenzyl)–amino acids: useful intermediates in peptide synthsis.' J. Pept. Sci. (1995), 1 pp. 11–25 (abstract).*
Database CAPLUS on STN, Acc. No. 1995:215364, Johnson et al., 'N,O–bisFmoc derivatives of N–(2–hydroxy–4–methoxybenzyl)–amino acids: useful intermediates in peptide synthesis' J. Pept. Sci. (1995), 1, pp. 11–25 (abstract). 1995.*

Database CAPLUS on STN, Acc. No. 1996:202869, Kitazawa et al., 'Skin preparations containing amino acid derivatives and polyhydric alcohols.' JP 08012547 (abstract). Jan. 16, 1996.*
Database CAPLUS on STN, Acc. No. 1995:478077, Kitazawa et al., 'Preparation of amino acid derivatives as antioxidants.' WO 9414755 A1 (abstract). Jul. 7, 1994.*
Database CAPLUS on STN, Acc. No. 1998:126640, Iwasaki et al., 'Skin preparations containing amino acids, anitoxidants, and metal–chelating agents.' JP 10053515 (abstract). Feb. 24, 1998.*
Database CAPLUS on STN, Acc. No. 1998:668110, Kitazawa et al., 'Preparation of amino acid derivatives and toiletry compositions for inhibition of active oxygen.' EP 869115 A2 (abstract). Oct. 7, 1998.*
S. Narasimhan, et al., Synlett, vol. 12, pp. 1321–1322, Chemoselectivity of Tetrabutylammonium Borohydride Towards Bifunctional Esters, Dec. 1998.
Derwent Publications, AN 1996–112611, JP 08 012547, Jan. 16, 1996.
H. M. Hassan, et al., J. Serb. Chem. Soc., vol. 63, No. 2, pp. 125–130, "Synthesis and Antimicrobial Activity of Some New Mannich Bases, N–(2–Hydroxy–1–Naphthyl)Amino Acid, Methyl Ester and Hydrazide Derivatives", 1998.
T. Johnson, et al., Journal of Peptide Science, vol. 1, pp. 11–25, "N, O–bisFmoc Derivatives of N–(2–Hydroxy–4–Methoxybenzyl)–Amino Acids: Useful Intermediates in Peptide Synthesis", 1995.

(List continued on next page.)

Primary Examiner—Brian Davis
(74) Attorney, Agent, or Firm—Oblon, Spivak, McClelland, Maier & Neustadt, P.C.

(57) ABSTRACT

Provided are an anti-inflammatory agent containing, as an active ingredient, at least one selected from amino acid derivatives represented by formula (I)

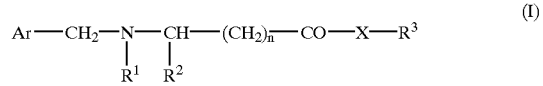

wherein Ar represents an optionally substituted 2-hydroxyaryl group, n is 0 or 1, $R^2$ represents a hydrogen atom or a side chain of an α-amino acid or β-amino acid, X represents —O— or —NH—, $R^1$ represents a hydrogen atom or a group that forms, together with $R^2$ and an adjacent atoms, a cyclic structure of pyroglutamic acid, and $R^3$ represents a hydrogen atom, an alkyl group having from 1 to 22 carbon atoms or an alkenyl group having from 2 to 22 carbon atoms, and salts thereof, and toiletries or skin external products containing the same. The anti-inflammatory agent of the invention inhibits expression of an inflammatory protein and activation of a gene transcription control factor that participates therein, and exhibits a good feeling upon use and a safety.

16 Claims, No Drawings

OTHER PUBLICATIONS

G. Ogier, et al., Biochemical Pharmacology, vol. 45, No. 8, pp. 1631–1644, "Contribution of 4–Methylthio–2–Oxobutanoate and Its Transaminase to the Growth of Methionine–Dependent Cells in Culture", 1993.

M. Morvin, et al., Acta Pharm. Jugost., vol. 32, No. 3, pp. 169–175, "Biologically Active Mannich Bases With Amino Acids", 1982.

D. S. Kemp, et al., J. Org. Chem., vol. 40, No. 23, pp. 3465–3466, "Peptide Bond Formation by the Prior Amine Capture Principle", 1975.

M. Sato, et al., The Journal of Rheumatology, vol. 23., No. 3, pp. 432–438, "Antioxidants Inhibit Tumor Necrosis Factor–α Mediated Stimulation of Interleukin–8, Monocyte Chemoattractant Protein–1, and Collagenase Expression in Cultured Human Synovial Cells", 1996.

J. Ruef, et al., Circulation, vol. 97, No. 11, pp. 1071–1078, "Induction of Rat Aortic Smooth Muscle Cell Growth by the Lipid Peroxidation Product 4–Hydroxy–2–Nonenal", Mar. 24, 1998.

S–R. Li, et al., Biological Signals, vol. 5, No. 5, pp. 263–274, "RT–PCR Study on the Effects of Minimally Modified Low–Density Lipoproteins and Probucol Treatment of Gene Expressions of Interleukin–1 and Platelet––Derived Growth Factor B–Chain in Human Peripheral Blood Mononuclear Bells", 1996.

Y. J. Suzuki, et al., Biochemistry and Molecular Biology International, vol. 32, No. 2, pp. 299–305, Inhibition of NF–kB Transcription Factor by Catechol Derivatives, Feb. 1994.

\* cited by examiner

AMINO ACID DERIVATIVES AND ANTI-INFLAMMATORY AGENTS

BACKGROUND OF THE INVENTION

1. Field of the Invention

The present invention relates to an anti-inflammatory agents that is useful for preventing, improving or treating inflammatory skin injuries or diseases, and skin external products and toiletries containing the same.

2. Description of the Related Art

In recent years, the causes of various skin injuries and diseases have been increasingly studied. For example, it is known that with respect to the causes of senescence, canceration, pigmentation and inflammation, inflammatory cytoklines such as IL-1α and TNF-α and extracellular matrix decomposition enzymes such as collagenase deeply participate therein (for example, "Oxidative Stress in Dermatology", Marcel Dekker, Inc., pp. 187–205, 1993). The expression of genes encoding these proteins is mainly controlled at a gene transcription level. Regarding the inflammatory proteins such as inflammatory cytokines and extracellular matrix decomposition enzymes, the expression thereof is controlled by transcription control factors such as NF-κB and AP-1 (for example, "Active Oxygen and Signal Transfer", Kodansha Scientific. pp. 37–46, 1996). Accordingly, when the expression of inflammatory proteins or the activation of transcription control factors participating therein can be inhibited, it is expected to prevent skin injuries and diseases.

For example, it is indicated that sulfur-containing antioxidants such as N-acetyl-L-cysteine and pyrrolidine dithiocarbamate inhibit NF-κB activation (for example, "Active Oxygen and Signal Transfer", Kodansha Scientific, pp. 37–46, 1996). N-acetyl-L-cysteine is reported to inhibit also AP-1 activation (for example, FEBS Letters, vol. 384, pp. 92–96, 1996). These compounds are however problematic in the feeling upon use owing to a peculiar odor derived from a sulfur atom present in the molecular structure thereof. Besides the sulfur-containing antioxidants, AP-1 activation and expression of extracellular matrix decomposition enzymes by retinoic acid (for example, Nature, vol. 379, pp. 335–339, 1996) and inhibition of NF-κB activation by a steroidal anti-inflammatory drug or a non-steroidal anti-inflammatory drug (for example, Bio Essays, vol. 18, pp. 371–378, 1996) have been reported. Nevertheless, retinoic acid has a side effect such as skin peeling, and a steroidal anti-inflammatory drug has a side effect such as steroidal dermatosis. Accordingly, the use thereof is limited. Although a non-steroidal anti-inflammatory drug is free from a systemic side effect encountered in the steroidal anti-inflammatory drug, a local side effect thereof has to be improved, and further, an effect of inhibiting inflammatory factor activation is unsatisfactory.

SUMMARY OF THE INVENTION

It is an object of the invention to provide an anti-inflammatory agents which inhibits expression of an Inflammatory protein and activation of a gene transcription control factor participating therein and which exhibits a good feeling upon use and a safety.

The present inventors have assiduously conducted investigations to achieve the object, and have consequently found that the object is achieved by using amino acid derivatives represented by the following formula (I) or salts thereof as an active ingredient. This finding has led to the completion of the invention.

That is, the invention relates to an anti-inflammatory agents containing, as an active ingredient, at least one selected from amino acid derivatives represented by formula (I)

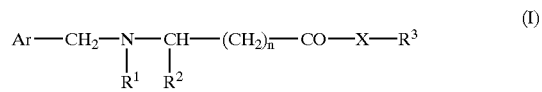

wherein
Ar represents an optionally substituted 2-hydroxyaryl group,
n is 0 or 1.
$R^2$ represents a hydrogen atom or a side chain of an α-amino acid or a β-amino acid,
X represents —O— or —NH—,
$R^1$ represents a hydrogen atom or a group that forms, together with $R^2$ and an adjacent atoms, a cyclic structure of pyroglutamic acid, and
$R^3$ represents a hydrogen atom, an alkyl group having from 1 to 22 carbon atoms or an alkenyl group having from 2 to 22 carbon atoms,
and salts thereof.

Further, the invention relates to an agent for preventing or treating inflammatory diseases, especially ultraviolet induction inflammatory diseases which agent contains at least one of the amino acid derivatives represented by formula (I) and the salts thereof.

Still further, the invention relates to a toiletry additive which is added as a toiletry component, this toiletry additive being composed of at least one of the amino acid derivatives represented by formula (I) and the salts thereof.

Furthermore, the invention relates to toiletries or skin external products containing at least one selected from the amino acid derivatives represented by formula (I) and the salts thereof. The toiletries of the invention are useful for preventing or improving inflammatory skin injuries, and the skin external products of the invention are useful for preventing or treating inflammatory diseases.

Of the compounds represented by formula (I), the compounds represented by formula (II) are novel compounds undescribed in the literature or publication.

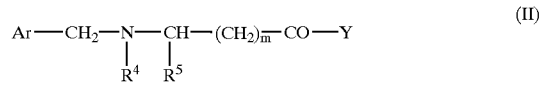

wherein
Ar may be substituted with 2-hydroxyaryl group,
m is 0 or 1,
$R^5$ represents a side chain selected from the group of alanine, phenylalanine, serine, cysteine. aspartic acid, cysteic acid, homocysteic acid, ornithine or histidine when m is 0 and , $R^5$ represents hydrogen atom when m is 1,
$R^4$ represents a hydrogen atom or a group that forms, together with $R^5$ and adjacent atoms, a cyclic structure of pyroglutamic acid, and
Y represents —$OR^6$, —$NHR^6$ or —$NH_2$, and
$R^6$ represents alkyl group having from 1 to 7 carbon atoms.

DETAILED DESCRIPTION OF THE INVENTION

The present invention will be explained in detail as follows.

In the compounds represented by formula (I), n is an Integer of 0 or 1. When n is 0, the compounds represented by formula (I) are β-amino acid derivatives. When n is 1, the compounds represented by formula (I) are β-amino acid derivatives.

When n is 0, $R^2$ in the amino acid derivatives represented by formula (I) is a hydrogen atom or a side chain of an α-amino acid. Examples of the side chain of the α-amino acid include side chain of acidic amino acids such as glutamic acid, aspartic acid, cysteic acid and homocysteic acid, neutral amino acids such as glycine, alanines valine, leucine, isoleucine, phenylalanine, tryptophan, threonine, serine, homoserine,tyrosine, dopa, cysteine, methionine, glutamine and asparagine, and basic amino acids such as lysine, ornithine, arginine and histidine. Side chains of neutral amino acids are preferable.

Further, when n is 1, $R^2$ may be a hydrogen atom or a side chain of a β-amino acid. As the β-amino acid, β-alanine is preferable.

In the amino acid derivatives represented by formula (I), $R^1$ is usually a hydrogen atom. However, $R^1$ can also form, together with $R^2$ and an adjacent atom, a cyclic structure: As the cyclic structure, a 2-pyrrolidone ring is preferable.

In this case, the compounds represented by formula (I) are pyroglutamic acid derivatives.

When an asymmetric carbon atom is present in the amino acid residue, the compounds may be either optically active compounds or racemic compounds.

The alkyl group in $R^3$ of formula (I) is a linear or branched alkyl group having from 1 to 22 carbon atoms, preferably from 1 to 18 carbon atoms, and it may have an unsaturated group in a part of a carbon chain. Examples of the alkyl group in the invention include methyl, ethyl, propyl, isopropyl, n-butyl, isobutyl, sec-butyl, tert-butyl, n-amyl, sec-amyl, tert-amyl, isoamyl, n-hexyl, cyclohexyl, n-heptyl, n-octyl, 2-ethylhexyl, nonyl, isononyl, decyl, isodecyl, undecyl, lauryl, tridecyl, isotridecyl, myristyl, cetyl, isocetyl, stearyl, isostearyl, behenyl groups and so on.

Further, the alkenyl group is a linear or branched alkenyl group having from 2 to 22 carbon atoms, preferably from 2 to 18 carbon atoms, more preferably from 5 to 18 carbon atoms which group may have at least one of carbon-carbon double bonds or carbon-carbon triple bonds as required. An alkenyl group derived from unsaturated fatty acids, such as an oleyl group, is preferable.

The 2-hydroxyaryl group in Ar group in formulae (I) and (II) is not particularly limited so long as it is an aromatic group having a hydroxyl group in the 2-position of a 5- or 6-membered aromatic ring. This aryl group is a monocyclic, polycyclic or fused-ring aromatic hydrocarbon group having at least one 6 -membered aromatic ring, or a monocyclic, polycyclic or fused-ring aromatic heterocyclic group having a 5- to 8-membered heterocyclic ring containing at least one of hetero-atoms such as nitrogen, oxygen and sulfur atoms, these groups having from 6 to 21 carbon atoms, preferably from 6 to 14 carbon atoms, more preferably from 6 to 12 carbon atoms.

These 2-hydroxyaryl groups may optionally be substituted unless it has an adverse effect on the activity of inhibiting inflammatory factor activation in the invention. At this time, examples of the substituent include the above-mentioned alkyl groups, alkoxy groups corresponding to the alkyl groups, alkoxycarbonyl groups corresponding to the alkyl groups, halogen atoms such as chlorine, fluorine and bromine, a hydroxyl group, a carboxyl group, nitro group and so on.

Specific examples of the optionally substituted 2-hydroxyaryl group of formulae (I) and (II) include 2-hydroxyphenyl, 2-hydroxy-1-naphthyl, 1-hydroxy-2-naphthyl, 2-hydroxy-4-methoxyphenyl, 2-hydroxy-3-methoxyphenyl, 5-bromo-2-hydroxyphenyl, 5-chloro-2-hydroxyphenyl, 2-hydroxy-5-nitrophenyl, 3,5-dibromo-2-hydroxyphenyl, 3,5-dichloro-2-hydroxyphenyl, 2,3-dihydroxyphenyl, 2,4-dihydroxyphenyl, 2,5-dihydroxyphenyl groups and so on.

In the compounds represented by formula (II), m is an integer of 0 or 1. When m is 0, the compounds represented by formula (II) are α-amino acid derivatives. When m is 1, the compounds represented by formula II) are β-amino acid derivatives.

When the compounds represented by formula (II) are α-amino acid derivatives (that is, when m is 0), examples of the amino acid include alanine, phenylalanine, serine, cysteine, aspartic acid, cysteic acid, homocysteic acid, ornithine and histidine. In this case, the substituent $R^5$ represents the side chain of the amino acid. When the compounds represented by formula (II) are β-amino acid derivatives (that is, m is 1), the amino acid is β-alanine.In this case, the substituent $R^5$ represents a hydrogen atom.

In the compounds represented by formula (II), the substituent $R^4$ is usually a hydrogen atom. However, $R^4$ can also form, together with $R^6$ and an adjacent atoms, a cyclic structure.

As the cyclic structure, a 2-pyrrolidone ring is preferable.

In this case, the compounds represented by formula (II) are pyroglutamic acid derivatives.

In the compounds represented by formula (II), Y is —$OR^6$, —$NHR^6$ or —$NH^2$ in which $R^6$ represents an alkyl group having from 1 to 7 carbon atoms. The alkyl group having from 1 to 7 carbon atoms in $R^6$ is a linear or branched saturated alkyl group. Examples of the alkyl group include methyl, ethyl, propyl, isopropyl, n-butyl, isobutyl, sec-butyl, tert-butyl, n-amyi, sec-amyl, tert-amyl, isoamyl and n-hexyl groups.

Accordingly, —$OR^6$ in the substituent Y is an alkoxy group having from 1 to 7 carbon atoms. Examples of the alkoxy group include methoxy, ethoxy, propoxy, isopropoxy, n-butoxy, isobutoxy, sec-butoxy, tert-butoxy, n-amyloxy, sec-amyloxy, tert-amyloxy, isoamyloxy and n-hexyloxy groups.

Further, —$NHR^6$ in the substituent Y is an N-alkylamino group, and it is an amino group substituted by the above-mentioned alkyl group.

Examples of the salts of the compounds represented by formulae (I) and (II) include inorganic acid salts such as a hydrochloride, a sulfate, a carbonate and a phosphate; and organic acid salts such as an acetate, a tartrate, a citrate, a p-toluenesulfonate, a glycolate, a malate, a lactate, a fatty acid salt, an acidic amino acid salt, pyroglutamate and so on. These salts may be used either singly or in combination. They may be incorporated as amino acid derivative salts, or amino acid derivative salts may be formed in a composition by incorporating amino acid derivatives and salts separately.

The amino acid derivatives represented by formula (I) can easily be formed by reacting a 2-hydroxy-aromatic aldehyde such as salicylaldehyde with an amino acid alkyl ester or an amino acid alkylamide in the presence or absence of a solvent and adding a hydrogenation agent such as sodium boron hydride to the reaction mixture.

Or it can also be formed by reacting a 2-hydroxy-aromatic aldehyde with an amino acid to form a Schiff base, adding thereto a hydrogenation agent such as sodium boron hydride to obtain an N-(2-hydroxy-aromatic-1-methylene) amino acid, and then esterifying or amidating the same.

Examples of the 2-hydroxy-aromatic aldehyde include, other than salicylaldehyde, 2-hydroxy-1-naphtoaldehyde, pyridoxal, 2-hydroxy-4-methoxybenzaldehyde, o-vanillin, 5-bromosalicylaldehyde, 5-chlorosalicylaldehyde, 5-nitrosalicylaldehyde, 3,5-dibromosalicylaldehyde, 3,5-dichlorosalicylaldehyde, 2,3-dihydroxybenzaldehyde, 2,4-dihydroxybenzaldehyde, 2,5-dihydroxybenzaldehyde and so on.

The anti-inflammatory agents of the invention can be administered either orally or parenterally. It is preferable to administer the same directly to an inflammatory factor activation system. Usually, it is preferable that the inhibitor is used by being incorporated into toiletries or skin external products. For examples when the inhibitor is incorporated into toiletries as an active ingredient to prevent or improve inflammatory skin injuries, it may be added in an amount of from 0.01 to 10% by weight, preferably from 0.1 to 5% by weight. Further, when the inhibitor is incorporated into skin external products as an active ingredient for preventing or treating inflammatory diseases, it may be added in an amount of from 0.01 to 50% by weight, preferably from 0.1 to 20% by weight. When the amount is less than 0.01% by weight, the activity of inhibiting inflammatory factor activation is not satisfactorily exhibited, and it is thus undesirable When the amount exceeds 50% by weight, the feeling upon use is problematic in that a dry and hard feeling is given to the skin. Thus, it is undesirable.

When the anti-inflammatory agent of the invention is incorporated into toiletries or skin external products, components that are generally used in toiletries or skin external products can be added, other than the anti-inflammatory agent of the invention, unless the effects of the invention are impaired. Examples of the components which are generally used in toiletries or skin external products include an oily material, a surfactant, a solvent, a wetting agent, a high-molecular substance, a powder product, a dyestuff, a flavor and so on.

Examples of the oily material include oils such as animal and vegetable oils, waxes such as lanolin, hydrocarbons such as paraffin, higher alcohols such as cetanol, higher fatty acids such as stearic acid, sterols, phospholipids such as lecithin, synthetic esters such as myristic acid, metallic soaps, a silicone oil and so on.

Examples of the surfactant include an anionic surfactant, a cationic surfactant, an ampholytic surfactant, a nonionic surfactant, an emulsifying agent, a solubilizing agent and so on.

Examples of the solvent include lower alcohols such as ethanol, ethers, glycerols, liquid nonionic surfactants, liquid oily materials, other organic solvents and water.

Examples of the wetting agent include polyhydric alcohols such as glycerol, salts of organic acids such as pyrrolidonecarboxylic acid, urea, mucopolysaccharides such as hyaluronic acid, and salts of amino acids such as proline.

Examples of the high-molecular substance include natural high-molecular compounds such as collagen. semisynthetic high-molecular compounds such as a partially deacetylated chitin, and synthetic high-molecular compounds such as carboxymethyl cellulose.

Examples of the powdery product include inorganic pigments such as talc, functional pigments such as synthetic mica, hybrid fine powders, pearlessence pigments such as titanium dioxide-coated mica, photochromic pigments, high-molecular powders such as a nylon powder, and organic powders such as Nε-lauroyl lysine.

Examples of the dyestuff include a legal tar dyestuff first group, a legal tar dyestuff second group, a legal tar dyestuff third group, a hairdye, a natural dyestuff and a mineral dyestuff.

Examples of the flavor include animal flavors such as musk, vegetable flavors such as a jasmine oil, synthetic flavors such as α-amylcinnamaldehyde, and mixed flavors.

The form of the toiletries or the skin external products containing the anti-inflammatory agent of the invention is not particularly limited. The toiletries or the skin external products may take the form of a solution, a paste, a gel, a solid or a powder. They may be used in an oil, a lotion, a cream, a milky lotion, a gel, a shampoo, a hair rinse, a hair conditioner, an enamel, a foundation, a lipstick, a cosmetic powder, a pack, an ointment, a tablet, an injection, a granule, a capsule, a perfume, a powder, an eau de Cologne, a toothpaste, a soap, an aerosol and a cleansing foam, as well as in an agent for preventing or improving skin aging, an agent for preventing or improving skin inflammation, a bath product, a hair tonic, a skin beauty lotion, an anti-sunburn agent, an agent for preventing or improving photodermatosis such as xeroderma pigmentosum or solar urticaria, an agent for preventing or improving photoallergy, an agent for preventing or improving photo-immunosuppression and an agent for preventing or improving skin irritation by injuries, chaps or cracks. Further, they can be used as an agent for preventing or treating various diseases caused by inflammatory factor activation, for example, rheumatoid diseases such as chronic rheumatism, arthritis, cutaneous diseases such as atopic dermatitis, contact dermatitis and psoriasis vulgaris, respiratory diseases such as bronchial asthma and bronchitis, inflammatory bowel diseases, acute or chronic hepatitis, acute or chronic nephritis, Mediterranean fever, and ischemic diseases such as myocardial infarction.

Moreover, other ordinary components in toiletries or skin external products can be added to the toiletries or the skin external products containing the anti-inflammatory agent of the invention unless the effects of the invention are impaired. The other ordinary components in toiletries or skin external products include an antiseptic, a disinfectant, an antioxidant, an ultraviolet absorber, a chelating agent, a discoloration preventing agent, a buffer, a drug for an acne, an agent for preventing dandruff and itching, an antiperspirant, a burn agent, an acaricidal and louse-killing agent, a keratin softening agent, a xerosis agent, an antiviral agent, a percutaneous absorption accelerator, hormones, vitamins, amino acids, peptides, proteins, an astringent, an anti-inflammatory agent, a refrigerant, a stimulant, components derived from animals and vegetables, a melanin synthesis inhibitor (whitening agent), antibiotics, an antifungal agent and a hair tonic.

The anti-inflammatory agent of the invention has an excellent activity of inhibiting inflammatory factor activation. Further, when the toiletries or the skin external products containing the anti-inflammatory agent of the invention are coated on the skin, these effectively remain on the skin, are hard to drop and have an excellent feeling upon use.

EXAMPLES

The invention is illustrated more specifically by referring to the following Examples. However, the invention is not limited thereto. In Examples, the amount was expressed in terms of % by weight.

Synthesis Example 1

Nine grams of glycine were dissolved in 60 ml of a 2N sodium hydroxide aqueous solution. To the solution were then added 12 ml of salicylaldehyde and 1.3 g of sodium boron hydride in this order. After the mixture was stirred for 1 hour, 12 ml of salicylaldehyde and 1.3 g of sodium boron hydride were added thereto again. After the resulting mixture was stirred at room temperature for 1 hour, the insoluble matter was separated through filtration, and the filtrate was extracted with diethyl ether. The extract was adjusted to a pH of 4 with hydrochloric acid to obtain 17 g of N-(2-hydroxybenzyl) glycine. Various N-(2-hydroxybenzyl) amino acids were obtained in the same manner.

Synthesis Example 2

L-serine (3.6 g) was dissolved in 17 ml of a 2N sodium hydroxide aqueous solution. To the solution were then added 3.6 ml of salicylaldehyde and 0.4 g of sodium boron hydride in this order. After the mixture was stirred for 1 hour, 3.6 ml of salicylaldehyde and 0.4 g of sodium boron hydride were added thereto again. After the resulting mixture was stirred overnight at room temperature, the insoluble matter was separated through filtration, and the filtrate was extracted with diethyl ether. The extract was adjusted to a pH of 7 with hydrochloric acid to obtain 4.8 g of N-(2-hydroxybenzyl)-L-serine. To 300 mg of the resulting N-(2-hydroxybenzyl)-L-serine were added 30 ml of ethanol to which a hydrogen chloride gas had been blown to saturation. The mixture was stirred overnight. The reaction solution was concentrated, and the resulting oil was purified through HPLC using Inertcil ODS-3 column (supplied by GL Science) in a high performance liquid chromatography (supplied by Hitachi) to obtain 114 mg of N-(2-hydroxybenzyl)-L-serine ethyl ester. Various N-(2-hydroxybenzyl) amino acid alkyl esters were obtained in the same manner. With respect to the novel compounds undescribed in the literature among these compounds, the results of the measurement of the mass spectrum are shown in Table 1.

TABLE 1

| Novel Compound Not-Described in Publication | mass spectral $(M + H^+)$ | |
|---|---|---|
| | A | B |
| N-(2-hydroxybenzyl)-L-alanine ethyl ester | 224 | 224 |
| N-(2-hydroxybenzyl)-D-alanine ethyl ester | 224 | 224 |
| N-(2-hydroxybenzyl)-L-serine ethyl ester | 240 | 240 |
| N-(2-hydroxybenzyl)-L-histidine ethyl ester | 290 | 290 |
| N-(2-hydroxybenzyl)-L-pyroglutamic acid ethyl ester | 264 | 264 |
| N-(2-hydroxybenzyl)-L-phenylalanine ethyl ester | 300 | 300 |
| N-(2-hydroxybenzyl)-L-alanine isopropyl ethyl ester | 238 | 238 |

A: measured
B: calculated

Synthesis Example 3

L-alanine (2.9 g) was dissolved in 20 ml of a 2N sodium hydroxide aqueous solution. To the solution were then added 3.5 ml of salicylaldehyde and 0.4 g of sodium boron hydride in this order. After the mixture was stirred for 1 hour, 3.5 ml of salicylaldehyde and 0.4 g of sodium boron hydride were added thereto again. After the resulting mixture was stirred at room temperature for 1 hour, the insoluble matter was separated by filtration, and the filtrate was extracted with diethyl ether. The extract was adjusted to a pH of 6 with hydrochloric acid to obtain 5.8 g of N-(2-hydroxybenzyl)-L-alanine. The resulting N-(2-hydroxybenzyl) -L-alantne ( 4.6 g) and 8.8 g of 1-dodecanol were added to 150 ml of toluene. A hydrogen chloride gas was then added thereto to saturation. Ten grams of molecular sieves were added thereto, and the mixture was stirred overnight. The insoluble matter was separated by filtration, and the filtrate was then concentrated. The resulting oil was dissolved in methylene chloride, and washed with a saturated aqueous solution of sodium chloride. The product was dried over magnesium sulfate, and then concentrated under reduced pressure to obtain 8g of N-(2-hydroxybenzyl)-L-alanine lauryl ester.

Various N-(2-hydroxybenzyl) amino acid alkyl esters were obtained in them same manner.

Synthesis Example 4

L-alanine laurylamide (25 g) and 1 g of sodium hydroxide were dissolved in 20 ml of methanol. To the solution were added 1.0 ml of salicylaldehyde and 0.1 g of sodium boron hydride in this order. After the mixture was stirred for 1 hour, 1.0 ml of salicylaldehyde and 0.1 g of sodium boron hydride were added thereto again in this order. After the resulting mixture was stirred overnight at room temperature, the insoluble matter was separated through filtration, and the residue was adjusted to a pH of 7 with hydrochloric acid. The oil was obtained through concentration under reduced pressure was dissolved in diethyl ether, washed with water, and then dried over magnesium sulfate. After the drying agent was separated through filtration, the filtrate was concentrated under reduced pressure to obtain 3 g of N-(2-hydroxybenzyl)-L-alanine laurylamide.

Various N-(2-hydroxybenzyl)amino acid alkyl amides were obtained in the same manner. With respect to the novel compounds undescribed in the literature among these compounds, the results of the measurement of the mass spectrum are shown in Table 2.

TABLE 2

| Novel Compound Not-Described in Publication | mass spectral $(M + H^+)$ | |
|---|---|---|
| | A | B |
| N-(2-hydroxybenzyl)-L-alanine ethyl ester | 223 | 223 |
| N-(2-hydroxybenzyl)-L-phenyl alanine ethyl amide | 299 | 299 |

A: measured
B: calculated

Test Example 1

Test for an Activity of Inhibiting NF-κB Activation

The test compound was added to human epidermal cells which had become confluent in a culture plate. Eighteen hours later, the culture solution was replaced with a phenol red-free medium. The cells were subjected to UV irradiation (UVB: 50 mJ/m$^2$)using Dermaray M-DMR-80 (supplied by Toshiba Iryo Yohin KK). After from 4 to 5 hours passed, the cells were recovered, and the nucleoproteins were extracted in a usual manner. With respect to the resulting nucleoproteins, NF-κB activated by gel shift assay was detected. The amount of NF-κB was determined by measuring a radioactivity of an NF-κB band using a bio-imaging analyzer BAS 2000 (supplied by Fuji Photo Film). The rate of inhibition of NF-κB activation on the test compound was calculated using formula (III).

$$\text{Rate (\%) of inhibition of NF-}\kappa\text{B activation}=\{1-(A_1-A_3)/(A_2-A_3)\}\times 100 \qquad (III)$$

wherein $A_1$: radioactivity of an NF-κB band in the addition of the test compound $A_2$: radioactivity of an NF-κB band in the non-addition of the test compound $A_3$: radioactivity of an NF-κB band when the test compound was not added, nor was UV irradiation conducted The results are shown in Table 3.

TABLE 3-1

| Test Compound | A | B |
|---|---|---|
| N-(2-hydroxybenzyl)glycine | 5 mM | 36 |
|  | 10 | — |
| N-(2-hydroxybenzyl)-L-alanine | 1 mM | 20 |
|  | 10 | — |
| N-(2-hydroxybenzyl)-L-serine | 10 mM | 17 |
|  | 30 | 34 |
| N-(2-hydroxybenzyl)-L-alanine ethyl ester | 0.2 mM | 68 |
|  | 2 | 77 |
| N-(2-hydroxybenzyl)-D-alanine ethyl ester | 1 mM | 90 |
|  | 2 | 87 |
| N-(2-hydroxybenzyl)-L-leucine ethyl ester | 1 mM | 84 |
|  | 2 | 57 |
| N-(2-hydroxybenzyl)-L-histidine ethyl ester | 1 mM | 69 |
|  | 2 | 72 |
| N-(2-hydroxybenzyl)-L-serine ethyl ester | 1 mM | 37 |
|  | 2 | 56 |
| N-(2-hydroxybenzyl)-L-pyroglutamic acid ethyl ester | 1 mM | 53 |
|  | 2 | 85 |
| N-(2-hydroxybenzyl)-L-tyrosine ethyl ester | 0.1 mM | 64 |
|  | 0.5 | 81 |

A: concentration
B: inhibitory rate (%)

TABLE 3-2

| Test Compound | A | B |
|---|---|---|
| N-(2-hydroxybenzyl)-L-alanine lauryl ester | 10 μM | 20 |
|  | 100 | 81 |
| N-(2-hydroxybenzyl)-D-alanine lauryl ester | 50 μM | 60 |
|  | 100 | 59 |
| N-(2-hydroxybenzyl)-L-leucine lauryl ester | 10 μM | 21 |
|  | 20 | 23 |
| N-(2-hydroxybenzyl)-L-serine lauryl ester | 10 μM | — |
|  | 50 | 79 |
| N-(2-hydroxybenzyl)-L-glutamic acid lauryl ester | 10 μM | — |
|  | 100 | 45 |
| N-(2-hydroxybenzyl)-L-tyrosine lauryl ester | 5 μM | 20 |
|  | 10 | 43 |
| N-(2-hydroxybenzyl)-L-alanine stearyl ester | 10 μM | 31 |
|  | 100 | — |
| N-(2-hydroxybenzyl)-L-alanine ethyl amide | 1 mM | 43 |
|  | 2 | 26 |
| N-(2-hydroxybenzyl)-L-phenylalanine ethyl amide | 0.5 mM | 102 |
|  | 1 | 47 |
| N-(2-hydroxybenzyl)-L-tyrosine ethyl amide | 1 mM | 72 |
|  | 2 | 28 |

A: concentration
B: inhibitory rate (%)

TABLE 3-3

| Test Compound | A | B |
|---|---|---|
| N-(2-hydroxybenzyl)-L-alanine lauryl amide | 10 μM | 53 |
|  | 20 | 65 |
| N-(2-hydroxybenzyl)-D-alanine lauryl amide | 10 μM | 29 |
|  | 50 | 97 |
| N-(2-hydroxybenzyl)-L-leucine lauryl amide | 10 μM | 40 |
|  | 50 | 89 |
| N-(2-hydroxybenzyl)-L-pyroglutamic acid lauryl amide | 50 μM | 75 |
|  | 100 | 74 |
| N-(2-hydroxybenzyl)-L-tyrosine lauryl amide | 10 μM | 39 |
|  | 100 | — |
| N-(2-hydroxybenzyl)-L-arginine lauryl amide | 10 μM | 16 |
|  | 50 | 28 |
| N-acetyl-L-cysteine | 10 mM | 23 |
|  | 30 | 55 |
| pyrrolidinedithiocarbamate | 5 μM | −9 |
|  | 10 | 9 |

A: concentration
B: inhibitory rate (%)

As shown in Table 3, the products all exhibit the activity of inhibiting NF-κB activation at lower concentrations than pyrrolidine dithiocarbamate, a known NF-κB activation inhibitor, and have a high activity of inhibiting inflammatory factor activation.

Test Example 2

Test for an Activity of Inhibiting AP-1 Activation

The test compound was added to human dermal fibroblasts which had become confluent in a culture plate. Eighteen hours later, the culture solution was replaced with a phenol red-free medium. The cells were subjected to UV irradiation (UVA: 20 J/cm$^2$) using Dermaray M-DMR-80 (supplied by Toshiba Iryo Yohin KK). After from 4 to 5 hours passed, the cells were recovered, and the nucleoproteins were extracted in a usual manner. With respect to the resulting nucleoproteins, AP-1 activated by gel shift assay was detected. The amount of AP-1 was determined by measuring a radioactivity of an AP-1 band using a bio-imaging analyzer BAS 2000 (supplied by Fuji Photo Film). The rate of inhibition of AP-1 activation on the test compound was calculated using formula (IV).

$$\text{Rate (\%) of inhibition of AP-1 activation}=\{1-(A_4-A_6)/(A_5-A_6)\}\times 100 \qquad (IV)$$

wherein $A_4$: radioactivity of an AP-1 band in the addition of the test compound $A_5$: radioactivity of an AP-1 band in the non-addition of the test compound $A_6$: radioactivity of an AP-1 band when the test compound was not added, nor was UV irradiation conducted The results are shown in Table 4.

TABLE 4-1

| Test Compound | A | B |
|---|---|---|
| N-(2-hydroxybenzyl)-L-alanin ethyl ester | 0.5 mM | 26 |
|  | 2 | — |
| N-(2-hydroxybenzyl)-L-histidine ethyl ester | 0.5 mM | 20 |
|  | 1 | 38 |
| N-(2-hydroxybenzyl)-L-serine ethyl ester | 0.5 mM | — |
|  | 1 | 73 |
| N-(2-hydroxybenzyl)-L-alanine isopropyl ester | 0.1 mM | 20 |
|  | 0.5 | 35 |

TABLE 4-1-continued

| Test Compound | A | B |
|---|---|---|
| N-(2-hydroxybenzyl)-L-alanine lauryl ester | 10 mM | 68 |
| | 50 | 66 |
| N-(2-hydroxybenzyl)-L-serine lauryl ester | 1 μM | 43 |
| | 10 | 49 |
| N-(2-hydroxybenzyl)-L-glutamic acid lauryl ester | 1 μM | — |
| | 10 | 33 |
| N-(2-hydroxybenzyl)-L-tyrosine lauryl ester | 1 μM | 19 |
| | 10 | 45 |
| N-(2-hydroxybenzyl)-L-alanine stearyl ester | 1 μM | 20 |
| | 5 | 48 |
| N-(2-hydroxybenzyl)-L-alanine ethyl amide | 1 mM | 52 |
| | 2 | 131 |

A: concentration
B: inhibitory rate (%)

TABLE 4-2

| Test Compound | A | B |
|---|---|---|
| N-(2-hydroxybenzyl)-L-phenylalanine ethyl amide | 0.5 mM | 34 |
| | 1 | 61 |
| N-(2-hydroxybenzyl)-L-alanine lauryl amide | 10 μM | 57 |
| | 20 | 56 |
| N-(2-hydroxybenzyl)-D-alanine lauryl amide | 1 μM | 14 |
| | 20 | 31 |
| N-(2-hydroxybenzyl)-L-pyroglutamic acid lauryl amide | 10 μM | — |
| | 100 | 42 |
| N-(2-hydroxybenzyl)-L-tyrosine lauryl amide | 10 μM | 40 |
| | 20 | 55 |
| N-(2-hydroxybenzyl)-L-alanine stearyl amide | 1 μM | 72 |
| | 5 | 47 |
| dexamethasone | 1 μM | 39 |
| | 10 | 34 |
| aspirin | 1 mM | −4 |
| | 5 | 14 |

A: concentration
B: inhibitory rate (%)

As shown in Table 4, the products all exhibit the activity of inhibiting AP-1 activation which exceeds that of aspirin, a non-steroidal anti-inflammatory drug, and have a high activity of inhibiting inflammatory factor activation.

Test Example 3
Test for an Activity of Inhibiting IL-1α Expression

The test compound was added to human epidermal cells which had become confluent in a culture plate. Eighteen hours later, the culture solution was replaced with a phenol red-free medium. The cells were subjected to UV irradiation (UVB: 50 mJ/cm$^2$) using Dermaray M-DMR-80 (supplied by Toshiba Iryo Yohin KK). After 24 hours passed, the culture solution was recovered, and the IL-1α concentration in the culture solution was measured using IL-1α·ELISA System (supplied by Amersham Corp.). The rate of inhibition of IL-1α expression on the test compound was calculated using formula (V).

Rate (%) of inhibition of IL-1α expression=$\{1-(B_1-B_3)/(B_2-B_3)\}\times 100$ (V)

wherein
$B_1$: IL-1α concentration in the addition of the test compound
$B_2$: IL-1α concentration in the non-addition of the test compound
$B_3$: IL-1α concentration when the test compound was not added, nor was UV irradiation conducted The results are shown in Table 5.

TABLE 5-1

| Test Componnd | A | B |
|---|---|---|
| N-(2-hydroxybenzyl)glycine | 5 mM | 26 |
| | 10 | 88 |
| N-(2-hydroxybenzyl)-L-alanine | 1 μM | 14 |
| | 10 | 100 |
| N-(2-hydroxybenzyl)-L-serine | 10 mM | 62 |
| | 30 | 70 |
| N-(2-hydroxybenzyl)-L-alanin ethyl ester | 0.2 mM | 61 |
| | 2 | 100 |
| N-(2-hydroxybenzyl)-L-serine ethyl ester | 0.1 mM | — |
| | 2 | 44 |
| N-(2-hydroxybenzyl)-L-pyroglutamic acid ethyl ester | 0.5 mM | 84 |
| | 1 | 55 |
| N-(2-hydroxybenzyl)-L-phenylalanine ethyl ester | 0.1 mM | 25 |
| | 1 | — |
| N-(2-hydroxybenzyl)-L-arginine ethyl ester | 0.5 mM | 65 |
| | 1 | — |
| N-(2-hydroxybenzyl)-L-alanine isopropyl ester | 0.1 mM | 36 |
| | 1 | 53 |

A: concentration
B: inhibitory rate (%)

TABLE 5-2

| Test Componnd | A | B |
|---|---|---|
| N-(2-hydroxybenzyl)-L-alanine lauryl ester | 10 μM | 23 |
| | 100 | 72 |
| N-(2-hydroxybenzyl)-D-alanine lauryl ester | 10 μM | 35 |
| | 50 | 31 |
| N-(2-hydroxybenzyl)-L-serine lauryl ester | 10 μM | 12 |
| | 100 | 31 |
| N-(2-hydroxybenzyl)-L-glutamic acid lauryl ester | 10 μM | 54 |
| | 100 | — |
| N-(2-hydroxybenzyl)-L-alanine stearyl ester | 1 μM | 25 |
| | 10 | 25 |
| N-(2-hydroxybenzyl)-L-alanine ethyl amide | 0.5 mM | 81 |
| | 1 | 99 |
| N-(2-hydroxybenzyl)glycine lauryl amide | 20 μM | 13 |
| | 50 | 45 |
| N-(2-hydrorybenzyl)-L-alanine lauryl amide | 10 μM | 69 |
| | 50 | 73 |
| N-(2-hydroxybenzyl)-D-alanine lauryl ainide | 20 μM | 25 |
| | 50 | 79 |
| N-(2-hydroxybenzyl)-L-leucine lauryl amide | 20 μM | 27 |
| | 50 | 79 |

A: concentration
B: inhibitory rate (%)

TABLE 5-3

| Test Compound | A | B |
|---|---|---|
| N-(2-hydroxybenzyl)-L-pyroglutamic acid lauryl amide | 10 μM | 25 |
| | 50 | 28 |
| N-(2-hydroxybenzyl)-L-tyrosiue lauryl amide | 1 μM | — |
| | 10 | 56 |
| N-(2-hydroxybenzyl)-L-alanine stearyl auiide | 5 μM | 30 |
| | 10 | 77 |
| dexamethasone | 10 μM | 48 |
| | 100 | 65 |
| pyrrolidinedithiocarbamate | 5 μM | −45 |
| | 10 | — |

A: concentration
B: inhibitory rate (%)

As shown in Table 5, the products all exhibit the activity of inhibiting IL-1α expression which is equal to or higher than that of dexamethasone, a steroidal anti-inflammatory drug, and have a high activity of inhibiting inflammatory factor activation.

Test Example 4

Test for an Activity of Inhibiting Collagenase Expression

The test compound was added to human dermal fibroblasts which had become confluent in a culture plate. Eighteen hours later, the culture solution was replaced with a phenol red-free medium. The cells were subjected to UV irradiation (UVA; 20 J/cm$^2$) using Dermaray M-DMR-80 (supplied by Toshiba Iryo Yohin KK). After 24 hours passed, the culture solution was recovered, and the collagenase concentration in the culture solution was measured using MMP-1α·ELISA System (supplied by Amersham Corp.). The rate of inhibition of collagenase expression on the test compound was calculated using formula (VI).

$$\text{Rate (\%) of inhibition of collagenase expression} = \{1-(B_4-B_6)/(B_5-B_6)\} \times 100 \quad (VI)$$

wherein $B_4$: collagenase concentration in the addition of the test compound $B_5$: collagenase concentration in the non-addition of the test compound $B_6$: collagenase concentration when the test compound was not added, nor was UV irradiation conducted The results are shown in Table 6.

TABLE 6-1

| Test Compound | A | B |
|---|---|---|
| N-(2-hydroxybenzyl)glycine ethyl ester | 10 μM | 39 |
| | 100 | 46 |
| N-(2-hydroxybenzyl)-D-alanin ethyl ester | 0.1 mM | — |
| | 0.5 | 108 |
| N-(2-hydroxybenzyl)-L-histidin ethyl ester | 0.1 mM | 44 |
| | 1 | 51 |
| N-(2-hydroxybenzyl)-L-serin ethyl ester | 0.5 mM | 30 |
| | 1 | — |
| N-(2-hydroxybenzyl)-L-alanine lauryl ester | 10 μM | 58 |
| | 50 | — |
| N-(2-hydroxybenzyl)-L-leucine lauryl ester | 10 μM | 21 |
| | 50 | — |
| N-(2-hydroxybenzyl)-L-glutamic acid lauryl ester | 1 μM | 53 |
| | 10 | 49 |
| N-(2-hydroxybenzyl)-L-tyrosine lauryl ester | 10 μM | 61 |
| | 50 | — |
| N-(2-hydroxybenzyl)-L-arginine lauryl ester | 10 μM | 52 |
| | 50 | — |
| N-(2-hydroxybenzyl)-L-alanine stearyl ester | 1 μM | 57 |
| | 5 | — |

A: concentration
B: inhibitory rate (%)

TABLE 6-2

| Test Compound | A | B |
|---|---|---|
| N-(2-hydroxybenzyl)-L-phenylalanine ethyl amide | 0.1 mM | 32 |
| | 0.5 | 27 |
| N-(2-hydroxybenzyl)-L-alanine lauryl amide | 1 μM | 57 |
| | 10 | — |
| N-(2-hydroxybenzyl)-L-leucine lauryl amide | 1 μM | 37 |
| | 10 | 60 |
| N-(2-hydroxybenzyl)-L-pyroglutamic acid lauryl amide | 10 μM | 23 |
| | 50 | 52 |
| N-(2-hydroxybenzyl)-L-tyrosine lauryl amide | 1 μM | 42 |
| | 10 | 84 |
| N-(2-hydroxybenzyl)-L-alanine stearyl amide | 1 μM | 72 |
| | 5 | — |
| dexamethasone | 1 μM | 27 |
| | 10 | 53 |
| aspirin | 1 mM | −197 |
| | 5 | −436 |

A: concentration
B: inhibitory rate (%)

As shown in Table 6, the products all exhibit the activity of inhibiting collagenase expression which exceeds that of aspirin, a non-steroidal anti-inflammatory drug, and have a high activity of inhibiting inflammatory factor activation.

Anti-inflammatory agents, toiletries and skin external products in Examples 1 to 16 were prepared in a usual manner.

Example 1  Tablet

| | |
|---|---|
| N-(2-hydroxybenzyl)-L-alaninelaurylamide | 10% by weight |
| lactose | 50 |
| starch | 20 |
| carboxymethylcellulose | 19 |
| magnesium stearate | 1 |

Example 2  Injection

| | |
|---|---|
| N-(2-hydroxybenzyl)-L-alanineethylester | 0.1% by weight |
| glucose | 2.0 |
| injection water | remainder |

Example 3  Ointment

| | |
|---|---|
| N-(2-hydroxybenzyl)glycineethylester | 1.0% by weight |
| urea | 20.0 |
| white vaseline | 15.0 |
| soft liquid paraffin | 6.0 |
| cetanol | 3.0 |
| stearylalcohol | 3.0 |
| glyceryl monostearate | 5.0 |
| flavor | suitable amount |
| antiseptic | suitable amount |
| buffer | 1.0 |
| purified water | remainder |

Example 4  Lotion (I)

| | |
|---|---|
| N-(2-hydroxybenzyl)-L-arginineethylester | 3.0% by weight |
| glycerol | 3.0 |
| sorbitol | 2.0 |
| polyoxyethylene(20)oleylether | 1.0 |
| ethanol | 15.0 |
| zinc p-phenolsulfonate | 0.2 |
| buffer | 0.1 |
| flavor | 0.2 |
| antiseptic | suitable amount |
| purified water | remainder |

Example 5  Lotion (II)

| | |
|---|---|
| N-(2-hydroxybenzyl)-L-tyrosineethylester | 0.5% by weight |
| glycerol | 4.0 |
| kaolin | 1.0 |
| calamine | 0.7 |
| camphor | 0.2 |
| ethanol | 14.0 |
| flavor | suitable amount |
| purified water | remainder |

Example 6  Cream

| | |
|---|---|
| N-(2-hydroxybenzyl)glycinelaurylester | 1.0% by weight |
| kojic acid | 1.0 |
| stearic acid | 2.0 |
| polyoxyethylene(25)cetylether | 3.0 |
| glycerylmonostearate | 2.0 |
| octyldodecanol | 10.0 |
| cetanol | 6.0 |
| reduced lanolin | 4.0 |
| squalane | 9.0 |
| 1,3-butylene glycol | 6.0 |

-continued

| | |
|---|---|
| polyethyleneglycol (1500) | 4.0 |
| antiseptic | suitable amount |
| flavor | suitable amount |
| purified water | remainder |

Example 7    Cream

| | |
|---|---|
| N-(2-hydroxybenzyl)-L-leucinelaurylamide | 1.0% by weight |
| solid paraffin | 5.0 |
| bees wax | 10.0 |
| vaseline | 15.0 |
| liquid paraffin | 41.0 |
| 1,3-butyleneglycol | 4.0 |
| glycerolmonostearate | 2.0 |
| polyoxyethylenesorbitan(20)monolaurate | 2.0 |
| borax | 0.2 |
| antiseptic | suitable amount |
| flavor | suitable amount |
| antioxidant | suitable amount |
| purified water | remainder |

Example 8    Milky lotion

| | |
|---|---|
| N-(2-hydroxybenzyl)glycineisopropylester | 2.0% by weight |
| retinol | 0.1 |
| bees wax | 0.5 |
| vaseline | 2.0 |
| glycerylmonostearate | 1.0 |
| polyethyleneglycolmonooleate | 1.0 |
| methylpolysiloxane | 2.0 |
| cetanol | 1.0 |
| squalane | 6.0 |
| carboxyvinylpolymer | 0.5 |
| 1,3-butyleneglycol | 4.0 |
| ethanol | 5.0 |
| antiseptic | suitable amount |
| flavor | suitable amount |
| purified water | remainder |

Example 9    Milky lotion

| | |
|---|---|
| N-(2-hydroxybenzyl)-D-alaninelaurylamide | 1.0% by weight |
| stearylalcohol | 0.5 |
| hardened palm oil | 3.0 |
| liquid paraffin | 35.0 |
| dipropyleneglycol | 6.0 |
| polyethyleneglycol (400) | 4.0 |
| sorbitan sesquioleate | 1.6 |
| polyoxyethylene(20)oleylether | 2.4 |
| carboxyvinylpolymer | 1.5 |
| potassium hydroxide | 0.1 |
| chelating agent | suitable amount |
| antiseptic | suitable amount |
| flavor | suitable amount |
| purified water | remainder |

Example 10    Gel

| | |
|---|---|
| N-(2-hydroxybenzyl)-L-alanineoctylamide | 0.05% by weight |
| liquid paraffin | 12.0 |
| glyceryl-tri(2-ethylhexanoate) | 50.0 |
| sorbitol | 10.0 |
| polyethyleneglycol(400) | 5.0 |
| acylmethyltaurine | 5.0 |
| polyoxyethylene(20)isocetylether | 10.0 |
| flavor | suitable amount |
| antiseptic | suitable amount |
| purified water | remainder |

Example 11    Beauty lotion

| | |
|---|---|
| N-(2-hydroxybenzyl)-L-alanineisopropylester | 0.5% by weight |
| dipropyleneglycol | 5.0 |
| polyethyleneglycol (400) | 5.0 |
| ethanol | 10.0 |
| carboxyvinylpolymer | 0.5 |
| sodium alginate | 0.5 |
| potassium hydroxide | 0.2 |
| polyoxyethylene(20)sorbitanmonostearate | 1.0 |
| sorbitolmonooleate | 0.5 |
| oleylalcohol | 0.5 |
| placenta extract | 0.2 |
| di-α-tocopherolacetate | 0.2 |
| flavor | suitable amount |

-continued

| | |
|---|---|
| antiseptic | suitable amount |
| discoloration preventing agent | suitable amount |
| purified water | remainder |

Example 12    Pack

| | |
|---|---|
| N-(2-hydroxybenzyl)-L-phenylalaninelaurylester | 3.0% by weight |
| polyvinylalcohol | 15.0 |
| carboxymethylcellulose | 5.0 |
| 1,3-butyleneglycol | 5.0 |
| ethanol | 12.0 |
| polyoxyethylene(20)oleylether | 0.5 |
| flavor | suitable amount |
| antiseptic | suitable amount |
| buffer | suitable amount |
| purified water | remainder |

Example 13    Foundation

| | |
|---|---|
| N-(2-hydroxybenzyl)glycinestearylamide | 5.0% by weight |
| liquid paraffin | 10.0 |
| polyoxyethylene(20)sorbitan monooleate | 3.5 |
| propyleneglycol | 3.0 |
| titanium oxide | 9.0 |
| kaolin | 24.0 |
| talc | 42.0 |
| color pigment | 3.0 |
| flavor | suitable amount |
| antiseptic | suitable amount |
| antioxidant | suitable amount |

Example 14    Cleansing foam

| | |
|---|---|
| N-(2-hydroxybenzyl)-L-serine | 0.5% by weight |
| N-lauroylglutamic acid triethanolamine salt | 25.0 |
| triethanolaminelaurate | 5.0 |
| polyoxyethylene(4)polyoxypropylene(11)butyl ether | 5.0 |
| ethanol | 3.0 |
| flavor | suitable amount |
| antiseptic | suitable amount |
| purified water | remainder |

Example 15    Shampoo

| | |
|---|---|
| N-(2-hydroxybenzyl)-L-serineethylester | 0.5% by weight |
| polyoxyethylene(3)laurylether triethanolaminesulfate | 3.0 |
| polyoxyethylene(3)laurylether sodium sulfate | 6.0 |
| sodium laurylsulfate | 1.5 |
| diethanolamidelaurate | 3.0 |
| lauryldimethylaminoacetic acid betaine | 2.5 |
| cationic cellulose | 0.2 |
| ethyleneglycoldistearate | 2.0 |
| flavor | suitable amount |
| antiseptic | suitable amount |
| chelating agent | suitable amount |
| buffer | suitable amount |
| purified water | remainder |

Example 16    Bath cube (granules)

| | |
|---|---|
| N-(2-hydroxybenzyl)-L-histidineethylester | 3.0% by weight |
| sodium sulfate | 44.0 |
| sodium hydrogencarbonate | 50.0 |
| borax | 2.0 |
| sodium carboxymethylcellulose | 1.0 |
| pigment | suitable amount |
| flavor | suitable amount |

What is claimed is:

1. An amino acid derivative represented by formula (II), or a salt thereof:

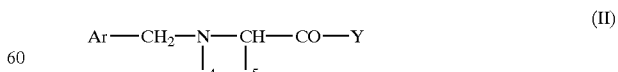

(II)

wherein
Ar represents a 2-hydroxyphenyl group,
$R^5$ represents a side chain selected from the group consisting of alanine, phenylalanine, serine, cysteine, cysteic acid, homocysteic acid, ornithine and histidine, $R^4$ represents a hydrogen atom or a group that forms, together with $R^5$ and an adjacent atom, a cyclic structure of pyroglutamic acid, Y represents —$OR^6$, —$NHR^6$, or —$NH_2$ and $R^6$ represents an alkyl group having from 1 to 7 carbon atoms.

2. The amino acid derivative of claim 1, wherein $R^5$ is a side chain of alanine.

3. The amino acid derivative of claim 1, wherein $R^5$ is a side chain of phenylalanine.

4. The amino acid derivative of claim 1, wherein $R^5$ is a side chain of serine.

5. The amino acid derivative of claim 1, wherein $R^5$ is a side chain of cysteine.

6. The amino acid derivative of claim 1, wherein $R^5$ is a side chain of cysteic acid.

7. The amino acid derivative of claim 1, wherein $R^5$ is a side chain of homocysteic acid.

8. The amino acid derivative of claim 1, wherein $R^5$ is a side chain of ornithine.

9. The amino acid derivative of claim 1, wherein $R^5$ is a side chain of histidine.

10. The amino acid derivative of claim 1, wherein $R^4$ is a hydrogen atom.

11. The amino acid derivative of claim 1, wherein $R^4$ together with $R^5$ and an adjacent atom forms a cyclic structure of pyroglutamic acid.

12. The amino acid derivative of claim 1, wherein Y is —$OR^6$.

13. The amino acid derivative of claim 1, wherein Y is —$NHR^6$.

14. The amino acid derivative of claim 1, wherein Y is —$NH_2$.

15. A composition comprising the amino acid derivative of claim 1, admixed with one or more carriers.

16. A method of treating inflammation comprising administering to a subject in need thereof the amino acid derivative of claim 1 in an amount effective to treat said inflammation.

* * * * *